(12) United States Patent
Cooper et al.

(10) Patent No.: US 11,553,865 B2
(45) Date of Patent: *Jan. 17, 2023

(54) BLADDER HEALTH MONITORING SYSTEMS AND RELATED METHODS AND DEVICES

(71) Applicant: University of Iowa Research Foundation, Iowa City, IA (US)

(72) Inventors: Christopher Cooper, Iowa City, IA (US); Ryan Steinberg, Iowa City, IA (US); Lewis Thomas, Chicago, IL (US); Eric Pahl, Ames, IA (US); Sanam Zarei, Coralville, IA (US); Kayla Jones, Chicago, IL (US)

(73) Assignee: University of Iowa Research Foundation, Iowa City, IA (US)

( * ) Notice: Subject to any disclaimer, the term of this patent is extended or adjusted under 35 U.S.C. 154(b) by 312 days.

This patent is subject to a terminal disclaimer.

(21) Appl. No.: 16/696,715

(22) Filed: Nov. 26, 2019

(65) Prior Publication Data

US 2020/0093412 A1    Mar. 26, 2020

Related U.S. Application Data

(63) Continuation of application No. 15/560,830, filed as application No. PCT/US2016/024057 on Mar. 24, 2016, now Pat. No. 10,506,965.

(Continued)

(51) Int. Cl.
*A61B 5/03* (2006.01)
*A61B 5/20* (2006.01)
*A61B 5/00* (2006.01)
*A61B 10/00* (2006.01)
*A61M 25/00* (2006.01)

(52) U.S. Cl.
CPC .............. *A61B 5/205* (2013.01); *A61B 5/202* (2013.01); *A61B 5/208* (2013.01); *A61B 5/6874* (2013.01); *A61B 5/03* (2013.01); *A61B 5/204* (2013.01); *A61B 5/6852* (2013.01);
(Continued)

(58) Field of Classification Search
CPC ....... A61B 5/205; A61B 5/208; A61B 5/6874; A61B 5/202; A61B 5/204; A61B 5/6852; A61B 5/03
See application file for complete search history.

(56) References Cited

U.S. PATENT DOCUMENTS

| | | |
|---|---|---|
| 7,004,899 B2 | 2/2006 | Tracey |
| 2004/0260163 A1 | 12/2004 | Kron et al. |

(Continued)

FOREIGN PATENT DOCUMENTS

| | | |
|---|---|---|
| CN | 101254141 A | 9/2008 |
| CN | 103948382 A | 7/2014 |
| WO | 2013143361 A1 | 10/2013 |

*Primary Examiner* — Chu Chuan Liu
(74) *Attorney, Agent, or Firm* — Dentons Davis Brown, P.C.; Matthew Warner-Blankenship

(57) ABSTRACT

The various embodiments disclosed here relate to systems, methods, and devices for monitoring bladder health. Certain implementations are directed to patients who require daily catheterization. The various embodiments have at least one tube coupled to a catheter, a pressure sensor, a pump, and a processor. Certain embodiments include a digital device with a software application capable of displaying the monitored readings.

19 Claims, 11 Drawing Sheets

Related U.S. Application Data

(60) Provisional application No. 62/137,633, filed on Mar. 24, 2015.

(52) U.S. Cl.
CPC ........ *A61B 10/007* (2013.01); *A61M 25/0017* (2013.01); *A61M 2025/0002* (2013.01)

(56) References Cited

U.S. PATENT DOCUMENTS

| | | | |
|---|---|---|---|
| 2006/0058702 A1* | 3/2006 | Christensen | A61B 5/205 600/561 |
| 2008/0027373 A1* | 1/2008 | Holte | G01L 7/20 604/27 |
| 2013/0066166 A1 | 3/2013 | Burnett et al. | |
| 2014/0200482 A1 | 7/2014 | Shi | |

* cited by examiner

Table 1: Comparison of Raw and Actual Pressure Values

| Tested Pressure | RAW 1 | RAW 2 | RAW 3 | Average |
|---|---|---|---|---|
| 0 | 105 | 99.6 | 99.9 | 101.5 |
| 10 | 260.1 | 252.2 | 255 | 255.767 |
| 20 | 403.4 | 393.9 | 393.8 | 397.033 |
| 30 | 543 | 543 | 537.3 | 541.1 |
| 40 | 687 | 685.5 | 685.4 | 685.967 |
| 50 | 829 | 828.4 | 829.7 | 829.033 |
| 60 | 969 | 961.1 | 967.6 | 965.9 |

Table 2: 16 French, 16 Inch

| Water Column | Average Sensor Reading | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|---|
| 70 | 1022.9 | 1023 | 1023 | 1023 | 1023 | 1023 | 1023 | 1023 | 1023 | 1022 | 1023 |
| 60 | 991.6333333 | | 999.5 | 998.8 | 993.3 | 993 | 993.8 | 997.4 | 985.1 | 978.5 | 985.3 |
| 50 | 853.58 | 897.7 | 855.6 | 852 | 850.2 | 847.3 | 849.8 | 854.8 | 843.1 | 838.6 | 846.7 |
| 40 | 708.38 | 766.2 | 711.8 | 705.3 | 703 | 704.2 | 704.2 | 701.9 | 700.4 | 688.7 | 698.1 |
| 30 | 563.36 | 606.4 | 562.6 | 563.8 | 558.2 | 569.8 | 557.6 | 558.8 | 552 | 546 | 558.4 |
| 20 | 415.76 | 450.9 | 423.9 | 411.5 | 411.9 | 417.1 | 413.9 | 414.5 | 409.5 | 399 | 405.4 |
| 10 | 268.05 | 289.7 | 278.7 | 269.2 | 264.4 | 269.5 | 265.4 | 270 | 259.9 | 253.2 | 260.5 |
| 0 | 118.46 | 108.7 | 109.1 | 128 | 122.8 | 125.2 | 123.8 | 124.5 | 112.7 | 112.8 | 117 |

FIG. 9

Table 3: 16 French, 6 Inch

| Water Column | Average Sensor Reading | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|---|
| 70 | 1023 | 1023 | 1023 | 1023 | 1023 | 1023 | 1023 | 1023 | 1023 | 1023 | 1023 |
| 60 | 1010.81 | 1005.3 | 1004.7 | 1018.8 | 1017.8 | 1014.3 | 1011.5 | 1012 | 1006.8 | 1010.2 | 1006.7 |
| 50 | 868.79 | 858.2 | 860.1 | 873.5 | 875.1 | 876 | 870.6 | 870.5 | 868.4 | 869.1 | 866.4 |
| 40 | 720.46 | 707 | 709.3 | 719.4 | 732.1 | 723.4 | 725.3 | 725.2 | 720.9 | 721.4 | 720.6 |
| 30 | 574.13 | 560.6 | 562.6 | 573.8 | 580.9 | 571.6 | 582.2 | 580.5 | 578 | 575.3 | 575.8 |
| 20 | 422.63 | 412.4 | 410.2 | 419.2 | 430.6 | 427.9 | 424.4 | 429.3 | 423.3 | 423.9 | 425.1 |
| 10 | 273.08 | 265.7 | 269 | 280.8 | 284.6 | 270.9 | 276.5 | 273.4 | 269.9 | 270.5 | 269.5 |
| 0 | 129.63 | 119 | 123.9 | 132.8 | 127.1 | 134 | 131.7 | 136 | 131.1 | 129.1 | 131.6 |

FIG. 10

Table 4: 14 French, 16 Inch

| Water Column | Average Sensor Reading | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|---|
| 70 | 1023 | 1023 | 1023 | 1023 | 1023 | 1023 | 1023 | 1023 | 1023 | 1023 | 1023 |
| 60 | 1022.93 | 1023 | 1023 | 1023 | 1023 | 1022.3 | 1023 | 1023 | 1023 | 1023 | 1023 |
| 50 | 886.28 | 888.5 | 895.1 | 882 | 886.5 | 885.1 | 883.3 | 886.1 | 886.6 | 887.7 | 881.9 |
| 40 | 740.05 | 743.7 | 744.8 | 736.5 | 744 | 738.6 | 734.5 | 740.2 | 737.9 | 743 | 737.3 |
| 30 | 587.62 | 585.9 | 593.3 | 583.4 | 597.3 | 587.8 | 588 | 590.8 | 586.9 | 585.1 | 577.7 |
| 20 | 436.74 | 435.4 | 435.2 | 438.1 | 435.9 | 436.5 | 433.9 | 438.7 | 438.8 | 435.1 | 439.8 |
| 10 | 277.62 | 274.6 | 276.8 | 275.5 | 276.5 | 278.5 | 274.7 | 277.7 | 280.1 | 280.1 | 281.7 |
| 0 | 137.68 | 130 | 136.2 | 139.3 | 136.7 | 137.7 | 138 | 140.9 | 138 | 140 | 140 |

FIG. 11

Table 5: 10 French, 10 Inch

| Water Column | Average Sensor Reading | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|---|
| 70 | 1023 | 1023.00 | 1023.00 | 1023.0 | 1023 | 1023 | 1023 | 1023 | 1023 | 1023 | 1023 |
| 60 | 989.78 | 988.00 | 987.10 | 992.4 | 985.5 | 996.4 | 991.5 | 990.3 | 987.3 | 987.5 | 991.8 |
| 50 | 846.21 | 844.10 | 841.60 | 844 | 844.9 | 852.8 | 843 | 851.3 | 847.9 | 845.8 | 846.7 |
| 40 | 699.24 | 698.20 | 696.50 | 692.9 | 695.9 | 706.3 | 698 | 704.9 | 698.9 | 697.1 | 703.7 |
| 30 | 548.52 | 543.70 | 548.90 | 549.3 | 545.3 | 549.8 | 549.3 | 548.2 | 549.3 | 544 | 557.4 |
| 20 | 400.28 | 400.20 | 392.10 | 398.9 | 414.2 | 400.6 | 401 | 398 | 399.4 | 398 | 402.4 |
| 10 | 250.55 | 250.00 | 247.20 | 250.4 | 250 | 250.1 | 255.8 | 252 | 249.9 | 251.3 | 248.6 |
| 0 | 106.74 | 100.00 | 100.00 | 111.2 | 105.3 | 108.1 | 107.3 | 108.5 | 108.9 | 108.7 | 109.4 |

FIG. 12

BLADDER HEALTH MONITORING SYSTEMS AND RELATED METHODS AND DEVICES

CROSS-REFERENCE TO RELATED APPLICATION(S)

This patent application is a continuation of U.S. patent application Ser. No. 15/560,830 filed on Sep. 22, 2017, which claims priority to International PCT Application No. PCT/US16/24057 filed on Mar. 24, 2016, which claims priority to U.S. Provisional Application No. 62/137,633 filed Mar. 24, 2015 and entitled "Bladder Health Monitoring Systems and Related Methods and Devices," all of which are hereby incorporated by reference in their entireties under 35 U.S.C. § 119(e).

FIELD OF THE INVENTION

The various embodiments herein relate to systems, methods, and devices for monitoring bladder health of a patient, including real-time monitoring of bladder health of patients who require daily catheterization, including, in some cases, clean, intermittent catheterization up to 15 times each day depending on the patient bladder size, function and/or urine production.

BACKGROUND OF THE INVENTION

Approximately 1.2 million people in the United States and 14 million worldwide suffer from neurogenic bladder—a condition in which an individual lacks normal bladder functionality due to an underlying brain, spinal cord, or pelvic nerve condition. When the nerves that innervate the bladder and urinary sphincters are compromised, the bladder and urinary sphincter fail to function in a normal way. For example; atonic bladder, overactive bladder, detrusor sphincter dysynergia, poorly compliant bladder and the like. In such cases, patients can have difficulty expelling urine and thus are reliant on intermittent bladder catheterization—including clean catheterization up to 15 times a day as discussed above—to empty the bladder of urine and relieve the pressure within the bladder. The passage of such a catheter can both prevent the bladder from becoming chronically over distended with weakened muscle wall or contracted with a tense and thickened wall. By improving bladder drainage, the risk of bladder and kidney infections can be reduced and harm to the kidney from high pressures urinary storage in the bladder can be prevented.

In a normal bladder, the bladder wall will be compliant, meaning that it will relax or stretch with filling (or increasing volume), thereby keeping the bladder at a low pressure. Accordingly, as used herein, "compliance" relates to the change in volume divided by the change in pressure. With the ensuing increase in urinary volume constrained in the bladder, the pressure within the bladder rises. When the pressure reaches a critically elevated level, such as above 40 cm $H_2O$, transmission of high pressures to the kidneys can occur, thereby potentially resulting in subsequent permanent kidney damage and/or failure that may require a kidney transplant or hemodialysis treatment for the remainder of their lives—a costly expense and grueling treatment that is necessary to control the condition of their failing/failed kidneys, including the electrolyte and fluid imbalances associated with kidney failure.

The current, known procedure utilized by clinicians to monitor the state of patients' bladders and the concomitant changes in bladder pressure with urinary volume readings is called Urodynamic Testing (UDS). This technique involves placing catheters in the bladder and/or rectum, and filling the bladder while measuring the compliance, pressure, and volume in the bladder. Drawbacks of UDS are that it requires an extensive amount of capital equipment, is not readily available in all clinics, is long in duration (a typical test requires 1-2 hours for completion), is expensive (around $4500 for testing and interpretation) and is contingent on factors related to the administration and interpretation of the test by the healthcare team. Another disadvantage is that the test is very invasive for patients, as patients have catheters placed in the bladder and rectum, the bladder is filled with fluid at a set rate while the pressure is continuously monitored, and the patients may be asked to urinate on command in front of the team administering the test. A further disadvantage is that it fails to provide a comprehensive summary of the bladder's condition—UDS only provides a snapshot of a single point in time (i.e. the time of test administration). Since UDS is normally done approximately once a year (though can be performed more or less frequently depending on the severity of the patient's disease), bladder pressure can increase between tests and thus bladder and/or kidney damage can go undetected by both physician and patient for prolonged periods of time. It is not uncommon for physicians to see patients with bladders and kidneys that have 'deteriorated' between their visits. This makes the initiation of any intervention for worsening bladder pressure (whether behavioral, medical, or surgery) a reactive intervention, rather than proactive.

There is a need in the art for improved systems, methods, and devices for monitoring bladder health of a patient.

BRIEF SUMMARY OF THE INVENTION

Discussed herein are various bladder health monitoring systems and devices that can be coupled to existing urinary catheters.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One Example relates to a bladder monitoring system including: a housing; a first elongate tube including a first lumen; a catheter coupling component disposed at a distal end of the first elongate tube, the catheter coupling component including an opening in fluid communication with the first lumen, where the catheter coupling component is constructed and arranged to be coupleable to a urinary catheter such that the opening is in fluid communication with a lumen of the urinary catheter, the urinary catheter being a single lumen catheter; a pressure sensor disposed within the housing and in fluid communication with the catheter coupling component via a proximal end of the first elongate tube; a processor disposed within the housing and operably coupled to the pressure sensor; a communications component operably coupled to the processor. Other embodiments of this aspect include corresponding computer systems, apparatus, and computer programs recorded on one or more computer storage devices, each configured to perform the actions of the methods.

Implementations may include one or more of the following features. The system further including a second elongate tube including a second lumen capable of fluidic communication with the catheter coupling component by way of a second opening. The bladder monitoring system further including a valve constructed and arranged to control fluid communication between the catheter coupling, the first elongate tube and the second elongate tube. The system where the pressure sensor is constructed and arranged to detect bladder pressure at the time of catheterization. The system where the communications component is constructed and arranged to wirelessly transmit the detected bladder pressure. The system where the first lumen is in fluid communication with the pressure sensor and the second lumen is in fluid communication with a pump constructed and arranged to evacuate a patient bladder. The bladder monitoring system where the pump is constructed and arranged to operate when in fluid communication with the catheter coupling. The bladder monitoring system where the pump is further constructed and arranged to transmit data relating to the flow rate to the processor. The bladder monitoring system further including a digital device including an application constructed and arranged to measure bladder compliance from the pressure sensor and flow rate. The bladder monitoring system where the digital device is constructed and arranged to display the bladder compliance measurement. The system where the pressure sensor is constructed and arranged to collect dynamic relative pressures in the catheter. Implementations of the described techniques may include hardware, a method or process, or computer software on a computer-accessible medium.

Another Example includes a bladder health monitoring system including: a bladder monitoring device including:. The bladder health monitoring system also includes a first elongate tube including a first lumen. The bladder health monitoring system also includes a catheter coupling component disposed at a distal end of the first elongate tube, the catheter coupling component including an opening in fluid communication with the lumen. The bladder health monitoring system also includes a pressure sensor in fluidic communication with the catheter coupling component. The bladder health monitoring system also includes a communications component. The bladder health monitoring system also includes a second elongate tube including a second lumen capable of fluidic communication with the catheter coupling component by way of a second opening. The bladder health monitoring system also includes a digital device constructed and arranged to wirelessly communicate with the bladder monitoring device via the communications component, the digital device including an application constructed and arranged to output pressure or volume readings from the bladder monitoring device. The bladder health monitoring system also includes where the catheter coupling component is constructed and arranged to couple to a single lumen urinary catheter such that the opening is in fluid communication with a lumen of the urinary catheter. Other embodiments of this aspect include corresponding computer systems, apparatus, and computer programs recorded on one or more computer storage devices, each configured to perform the actions of the methods.

Implementations may include one or more of the following features. The bladder health monitoring system where the bladder monitoring device further including the communications component is a transceiver. The bladder health monitoring system where the pressure sensor is constructed and arranged to detect pressure within the lumen and transmit data relating to the pressure to the processor. The bladder health monitoring system further including a pump in fluidic communication with the catheter coupling component and constructed and arranged to evacuate a patient bladder; The bladder health monitoring system where the pump is further constructed and arranged to detect the volumetric flow rate of the fluid within the lumen and transmit data relating to the volumetric flow rate to the processor. The bladder health monitoring system where the application is constructed and arranged to measure bladder compliance from the pressure sensor and volumetric flow rate. The bladder health monitoring system where the digital device is constructed and arranged to display the bladder compliance measurement. The bladder health monitoring system further including a valve constructed and arranged to control fluid communication between the catheter coupling, the first elongate tube, and the second elongate tube. Implementations of the described techniques may include hardware, a method or process, or computer software on a computer-accessible medium.

A further Example includes a catheterization bladder health monitoring system, including: a housing; a first elongate tube including a first lumen disposed through the housing; a single lumen catheter coupling component disposed at a distal end of the elongate tube and outside the housing, the catheter coupling component including an opening in fluid communication with the lumen; a communications component; a second elongate tube including a second lumen capable of fluidic communication with the catheter coupling component by way of a second opening; and a pump, where: the catheter coupling component is constructed and arranged to be couple to a urinary catheter such that the opening is in fluid communication with a lumen of the urinary catheter, the urinary catheter being a single lumen catheter, and the bladder health monitoring system is constructed and arranged to sense bladder pressure. Other embodiments of this aspect include corresponding computer systems, apparatus, and computer programs recorded on one or more computer storage devices, each configured to perform the actions of the methods.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 9 shows exemplary measured values from a 16 inch long, 16 French gauge catheter FIG. 10 shows additional exemplary measured values from a 16 inch long, 16 French gauge catheter FIG. 11 shows exemplary measured values from a 16 inch long, 14 French gauge catheter FIG. 12 shows exemplary measured values from a 10 inch long, 10 French gauge catheter

DETAILED DESCRIPTION

Figure 1:
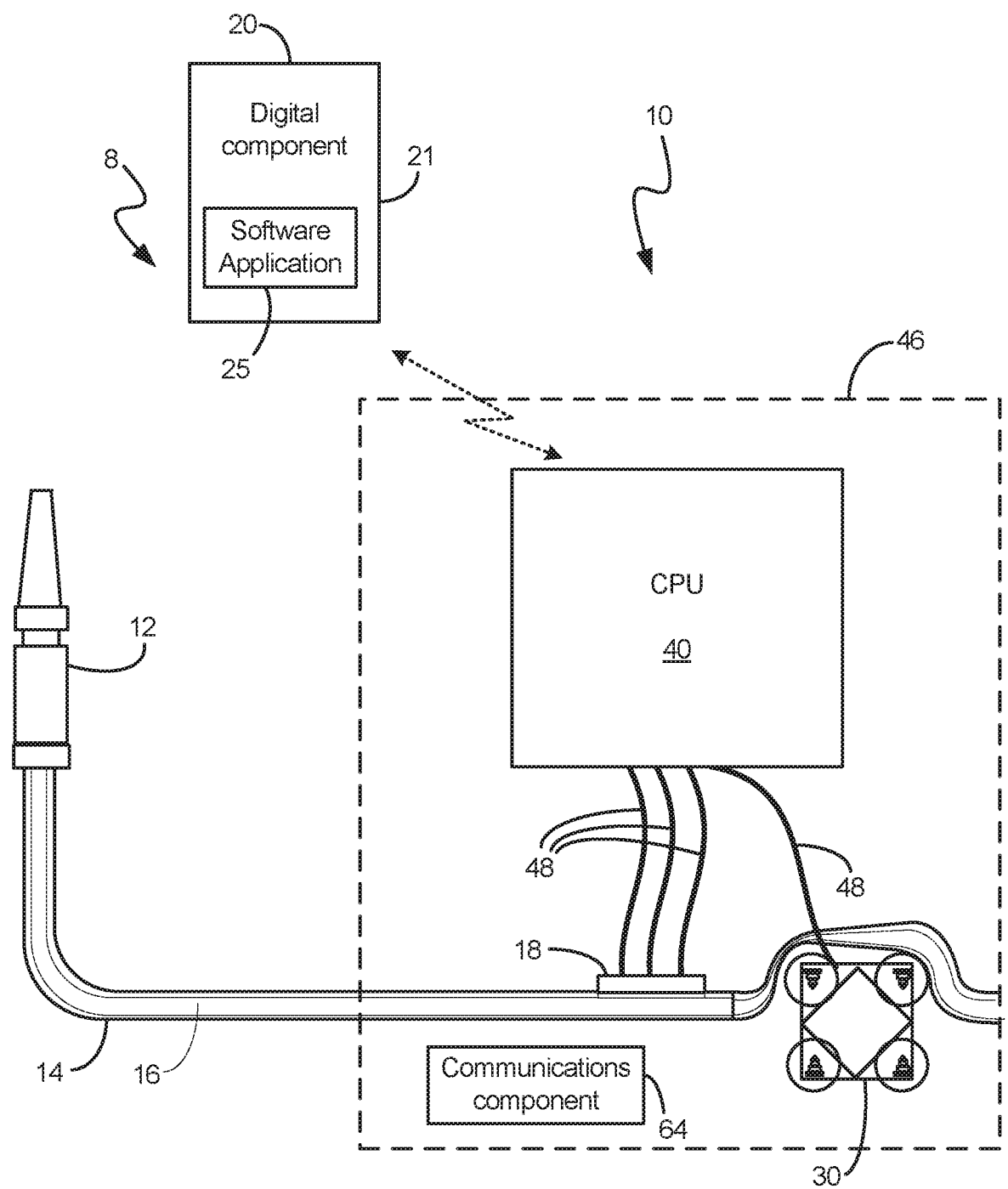
FIG. 1 shows the processor coupled to a pressure sensor and pump, in communication with a digital component, according to an exemplary embodiment.

The various embodiments disclosed herein relate to methods, systems, and devices for monitoring bladder health, especially in a patient with a catheterized bladder. In certain implementations, the patient can be intermittently catheterized. As used herein, "bladder health" can include monitoring in real-time the pressures, volumes, and compliance of urinary bladders, as well adherence to catheterization schedules, in patients who require catheterization, including intermittent catheterization from 0-15 times per day depending on the patient's bladder underlying condition, bladder structure, bladder function, urine volume production and/or fluid consumption. The various embodiments provide for noninvasively monitoring bladder pressure and volume readings in real time. Further, various implementations promote faster fluid flow from the bladder than by gravitational urinary flow.

In certain implementations, the various methods, systems, and devices herein will permit data collection, including bladder pressure at catheter insertion, volume of expelled urine, bladder compliance calculation, the time and date and other relevant information (collectively "data"). Some embodiments provide for this digital information to be recorded and transmitted to an electronic device. In various implementations, the electronic device is configured to store the data and synchronize the data with a secured server or electronic health record system. Using pre-set thresholds, the identification of harmful pressures, volumes, or catheter frequencies can then be addressed by clinicians through therapeutic interventions to prevent bladder injury. The various implementations can speed up the time required for patients to empty their bladders, for example, by way of a pump.

Prior to the invention of the various embodiments disclosed herein, there was no similar portable, handheld, in-home, or other non-UDS device available for patients to monitor their own "bladder health." As described above, known methods to assess bladder health involve the use of invasive, expensive, and time-consuming techniques that are completed on an annual basis in a hospital or clinic setting and therefore do not provide real-time monitoring. The various implementations disclosed herein provide patients and clinicians with a device that will regularly monitor the bladder in a non-invasive, time-efficient, and inexpensive manner while providing patients and their caregivers with a faster way to eliminate urine, freeing up time for both parties.

As shown in FIGS. 1-3C and FIGS. 4-6, various embodiments relate to a system 8 having a physical device component 10 and a digital component 20. The physical device component 10 is a bladder monitoring device 10 that can couple to a patient's urinary catheter and thereby measures the pressure in the bladder (shown at box 6 in FIG. 4) at the time of urinary catheter insertion as well as the volume obtained from catheterization and the time and date of each catheterization. The digital component 20 is a separate system or processor running a software application 25 such as a mobile device application, electronic medical health records system, or other electronic database or records system that is configured to interface with the digital component 20. This software application 25 (also referred to herein as an "algorithm" or "module") that has flexible function settings for extracting information for compiling, packaging, processing, evaluating the various bladder health readings of the system 8 for analysis and display.

Figure 2A:
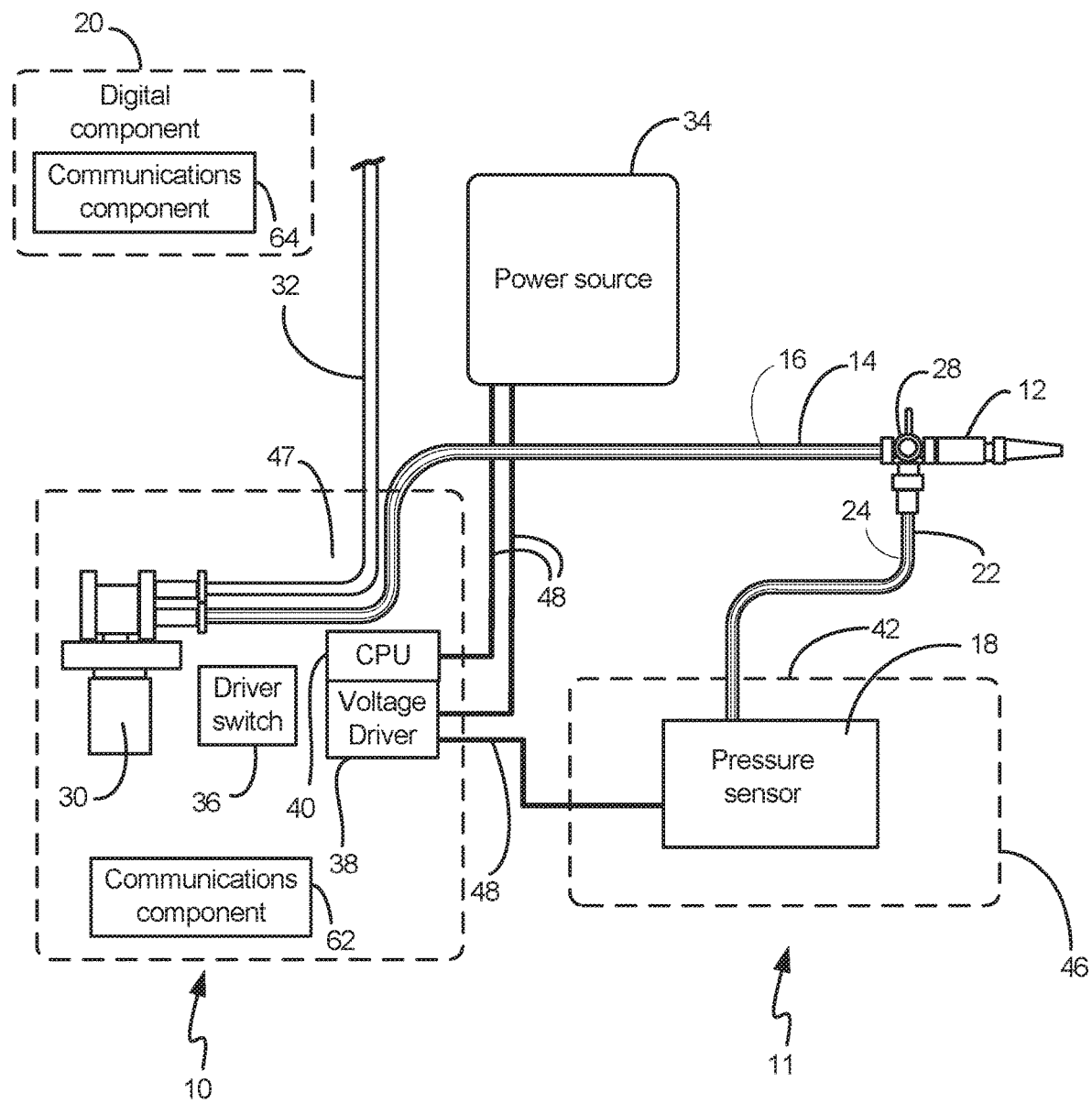
FIG. 2A shows an exemplary embodiment in which the pressure sensor and the processor are contained in separate casings
Figure 2B:
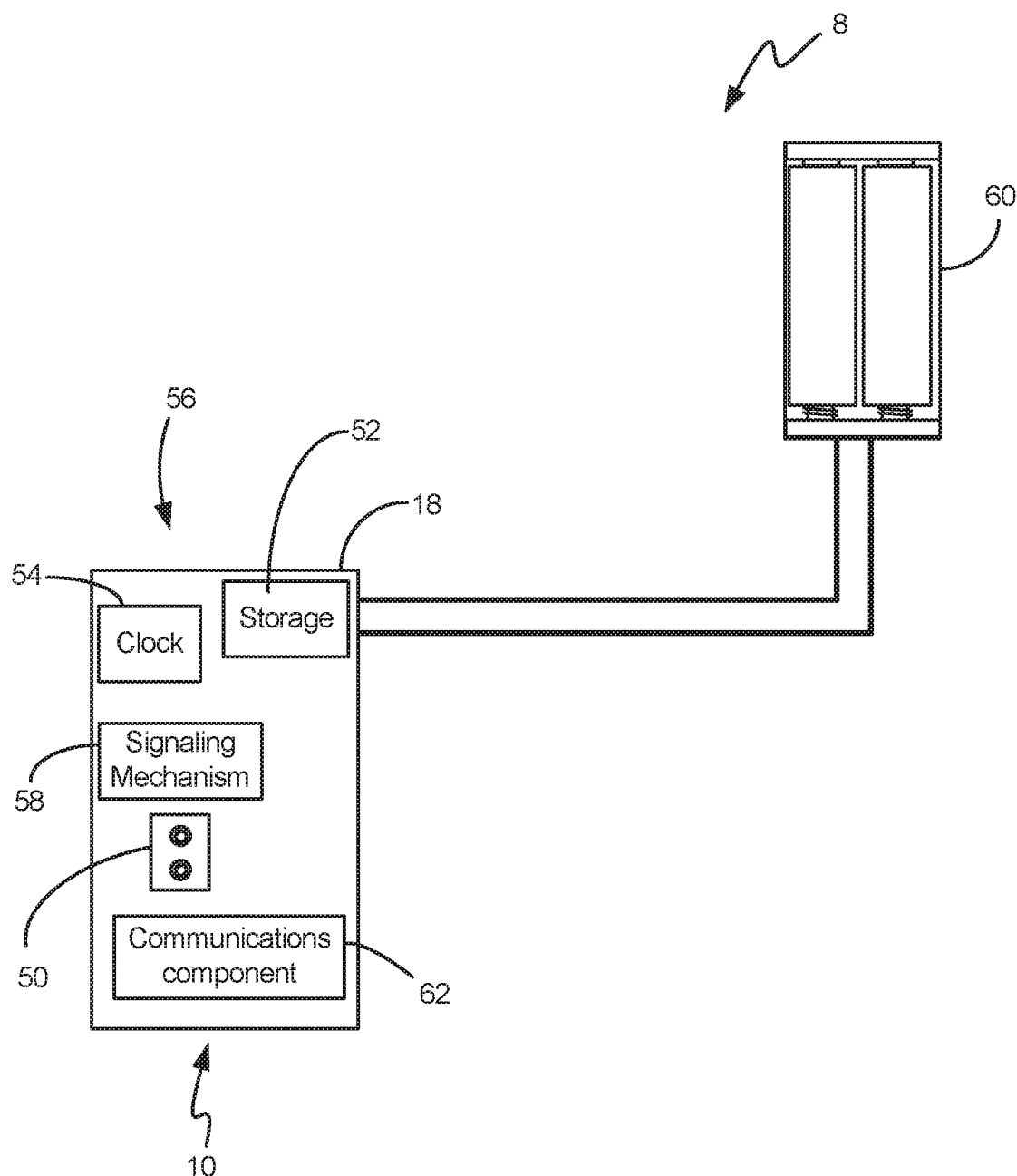
FIG. 2B shows components of the pressure sensor, according to an exemplary embodiment.
Figure 4:
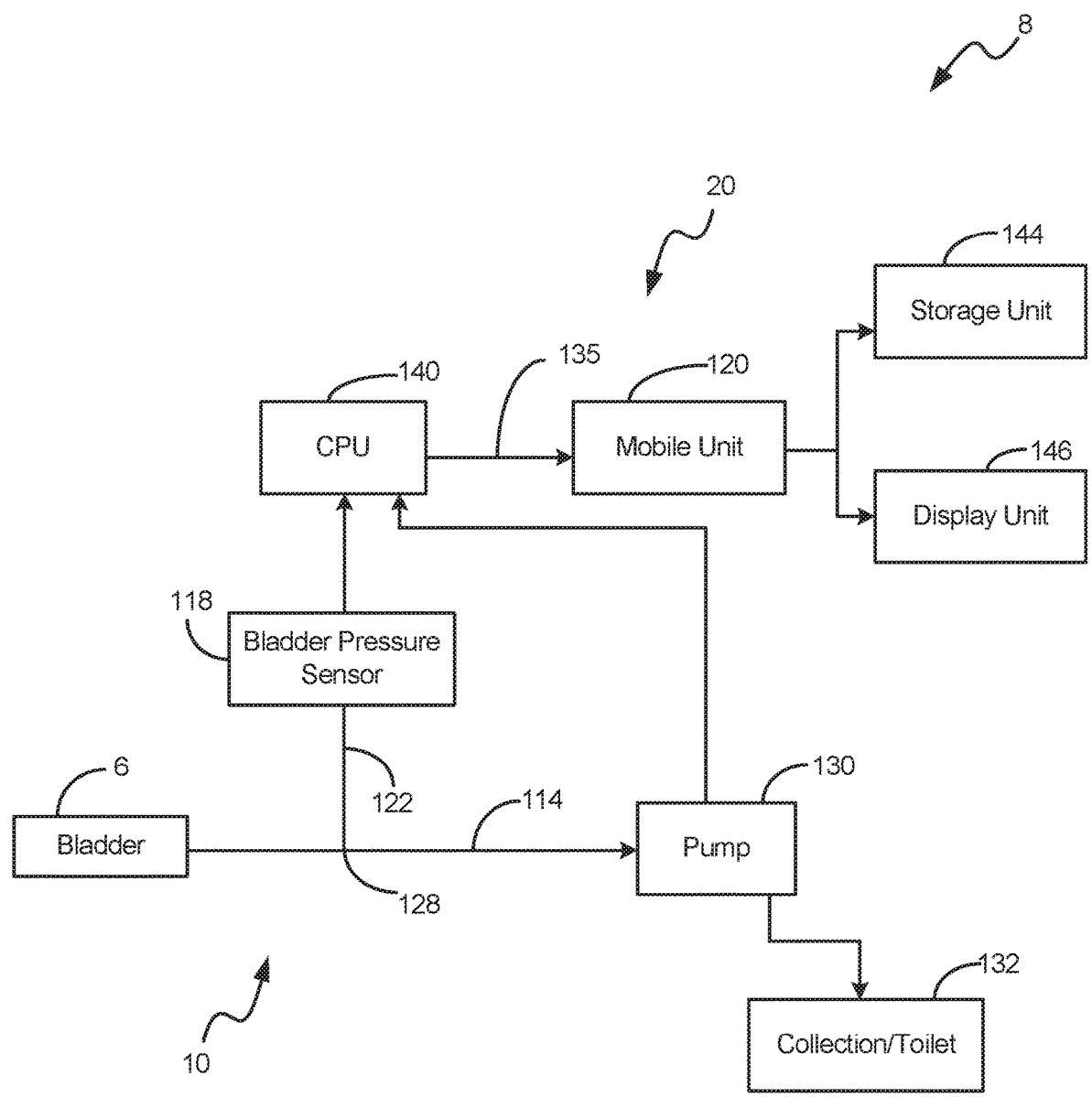
FIG. 4 shows a chart to describe the interaction between the device and patient, according to an exemplary embodiment FIG. 5 describes the device operation, according to an exemplary embodiment FIG. 6 describes the digital component operation, according to an exemplary embodiment

In various implementations, the physical device component 10 and digital component 20 can consist of multiple components distributed variously. For example, the device component may be distributed over multiple separate components (as shown in FIGS. 2A-B). Likewise, the digital component 20 can also consist of multiple components and be housed with portions of the device component 10 or elsewhere. As shown in FIG. 4, the physical device component 10 and digital component 20 are operationally integrated around a CPU 40, such that readings from the device component 10 are processed, stored and displayed by way of the digital component 20.

In FIG. 1, the digital component 20 is depicted as a mobile device 21 that contains an appropriate application for use in the system 8. As such, as shown variously in the drawings, the device 10 can record and store the digital information (pressure, volume, and time and date readings) and wirelessly transmit the information to the digital component 20 through paired communications components 62, 64. In one embodiment, the mobile device application is an iPhone® app and the wireless transmission occurs via Bluetooth™ or WiFi. In alternate embodiments, such as those depicted in FIGS. 2A-3B, the digital component 20 can comprise physical storage media, such as an SD card, as discussed below.

As shown in the embodiments of FIGS. 2A-3C, the device 10 has a catheter coupling component 12 at a distal end of the device 10. In one implementation, the catheter coupling component 12 is coupleable directly to the end of a urinary catheter (not shown). For example, in one specific embodiment, the coupling component 12 is a tapered coupling component 12 that can be positioned in the catheter, as would be apparent to a skilled artisan. In this implementation, the coupling component 12 is coupled to a tube 14 having a lumen 16. When the component 12 is coupled to a catheter, the lumen 16 is in fluid communication with the lumen of the catheter (not shown).

In this embodiment, the device 10 has a pressure sensor component 18 that is positioned in and through the wall of the tube 14 such that a portion of the sensor component 18 is positioned within the lumen 16 of the tube 14. As such, the sensor component 18 can come into contact with fluid in the lumen 16 and thus is in fluid communication with the urinary catheter tubing via the catheter coupling component 12. According to one embodiment, the pressure sensor component 18 is configured to detect pressure—for example static or dynamic fluid pressure—and transmit the data relating to the pressure readings to the processor 40 (discussed further below). In exemplary embodiments, and as described below in relation to Table 1, the pressure sensor component 18 can collect dynamic relative pressures in the catheter. The In various embodiments, and as shown in FIGS. 1-3B, the device 10 also has a pump 30 in fluid communication with the lumen 16 of the tube 14. In one implementation, the pump 30 is configured to urge the fluid proximally along the lumen 16 of the tube 14. In one specific example of a pump 30, the tube 14 is positioned through the pump 30 and the pump 30 is configured to repeatedly compress and expand the tube 14, thereby creating a suction action that urges the fluid proximally along the lumen 16. According to one embodiment, the fluid is urged proximally in the lumen 16 until it is expelled from a proximal end 32 of the tube 14 into a collection vessel or container (shown in FIG. 4 at box 132) for removal.

Figure 3A:
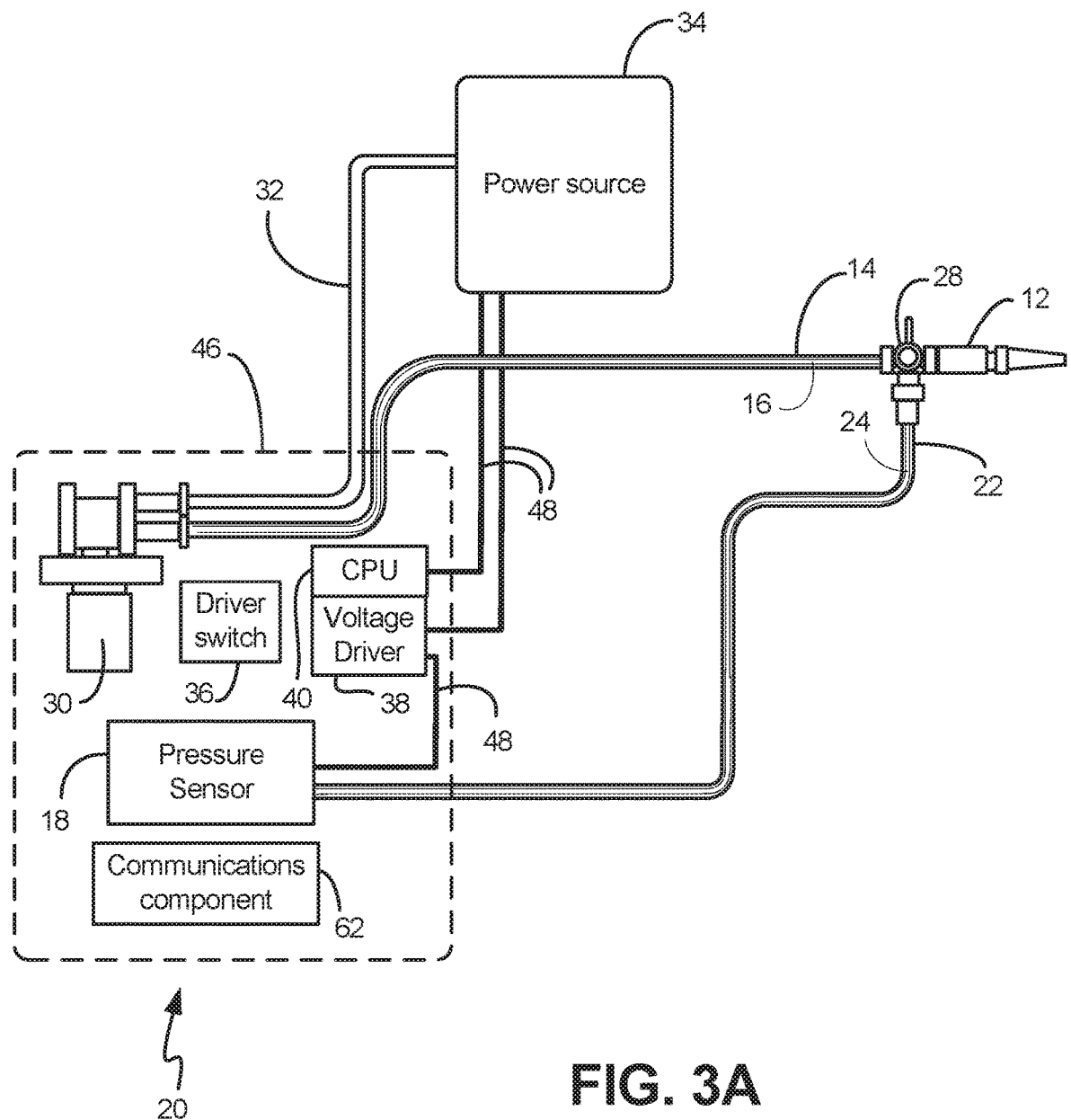
FIG. 3A shows an exemplary embodiment in which the pressure sensor and the processor are contained in a single casing
Figure 3B:
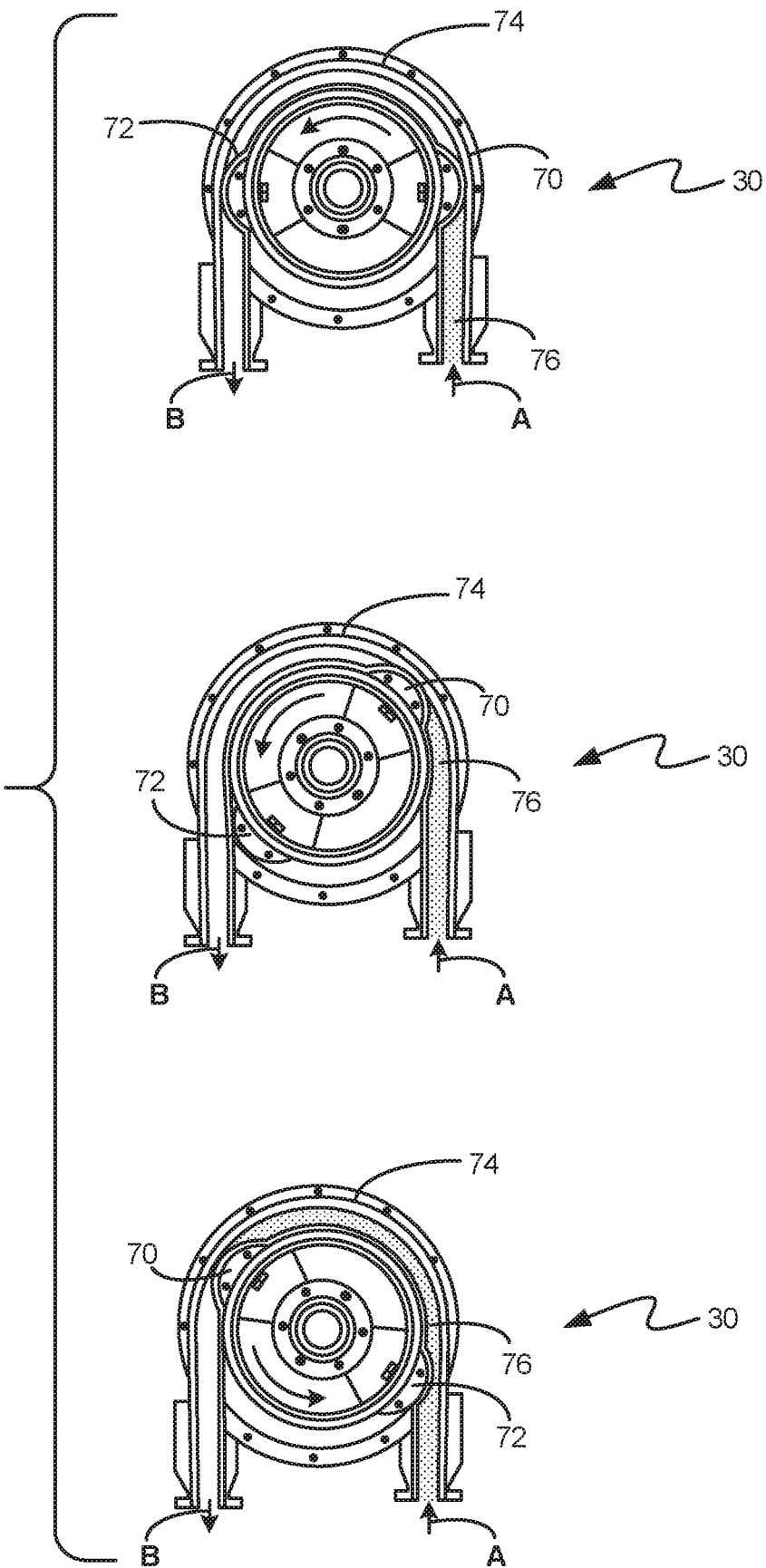
FIG. 3B shows the measurement and flow/acceleration of fluid through a peristaltic pump, according to an exemplary embodiment

As shown in the embodiments of FIGS. 1 and 3A-B, the pressure sensor component 18, pump 30, and processor 40 can be disposed within a container or housing 46. The housing 46 can help prevent damage to these components 18, 30, 40 during use and further can help to maintain structural integrity of the overall device 10. The housing 46 can be opened to replace the batteries held within the bladder health monitoring system 8. Alternatively, as shown in the embodiments of FIGS. 2A-B, various aspects of the system 8 may be distributed separately in a first housing 46 and a second housing 47. These implementations can provide certain advantages in terms of form and installation, as would be apparent to one of skill in the art. Other configurations are possible.

Figure 3C:
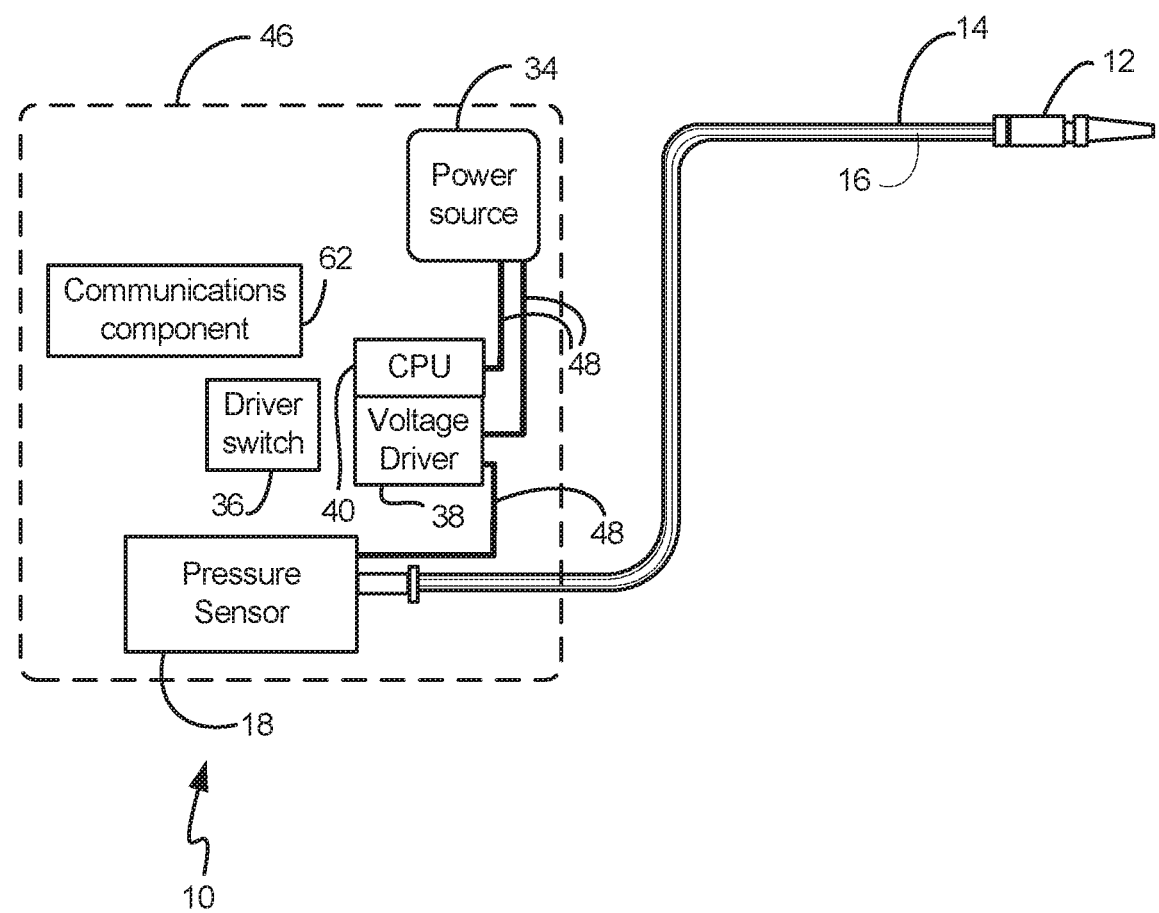
FIG. 3C shows another exemplary embodiment for taking pressure readings

As shown in FIG. 3C, in certain embodiments, the physical device 10 may not have a pump, but instead simply be a pressure sensing device 10. In various implementations, the pressure sensing device 10 has a coupling component 12, an elongate tube 14 with a lumen 16 in fluid communication with a pressure sensor component 18. A processor or CPU 40, battery 34 and communications component 62 are also disposed within the housing 46, so as to allow the patient to take pressure readings from a catheter (not shown) as described in detail herein. These readings can be transmitted out to a digital device 20 having another communications component 62 and used to monitor patient bladder health. As would be appreciated by one of skill in the art, these implementations can be used with any of the other components discussed herein.

Returning to the implementation of FIGS. 2A-3B, a second tube 22 and second lumen 24 may be provided and adjoined to the first tube 14 by way of a valve 28, such as a stopcock. In these implementations, the first tube 14 is in hermetic and fluidic communication with the pump 30, and the second tube 22 is in hermetic and fluidic communication with the pressure sensor component 18, such that the communication with the coupling component 12 can be controlled by the valve 28. A power source 34 such as a battery or outlet power can be used to provide electricity to the device 10.

In these embodiments, after attaching the coupling component 12 to the catheter (not shown), the valve 28 can be set in a "closed" position, such that the pressure sensor component 18 is in hermetic and fluidic communication with the catheter through the coupling 12, such that the pressure of the bladder can be assessed. In a subsequent step, the valve 28 can be toggled to an "open" position to put the coupling 12 in communication with the first tube 14 and lumen 16. Contemporaneously, the pump 30 can be activated, as described further below.

Accordingly, as shown in FIG. 4, in certain implementations, the patient's bladder (box 6) is in fluidic communication with the pump (box 130) and sensor (box 118) by way of the first tube (line 114) and second line (line 122), respectively, as dictated by the valve (junction 128). In these implementations, the sensor (box 118) is in electronic communication with a processor, or CPU (box 140), which in turn is in communication with a mobile unit (box 120). The mobile unit (box 120) can have a storage unit (box 144) and a display unit (box 146). Further, in these implementations, the pump (box 130) is also in electronic communication with the CPU (box 140) to transmit data (line 135) such as volume data to the CPU (box 140) and mobile unit (box 120). As discussed above, the data transmission (line 135) can occur wirelessly through paired communications components 62, 64—such as by Bluetooth™ or WiFi—or by way of a physical connection, such as a wired connection (not shown) or digital storage media, such as an SD card (shown in FIG. 2B at 52) or jump drive. Further, in exemplary embodiments, the time and date of each time the device system 8 is connected to a catheter and is in use is recorded by way of the CPU (box 140).

Figure 5:
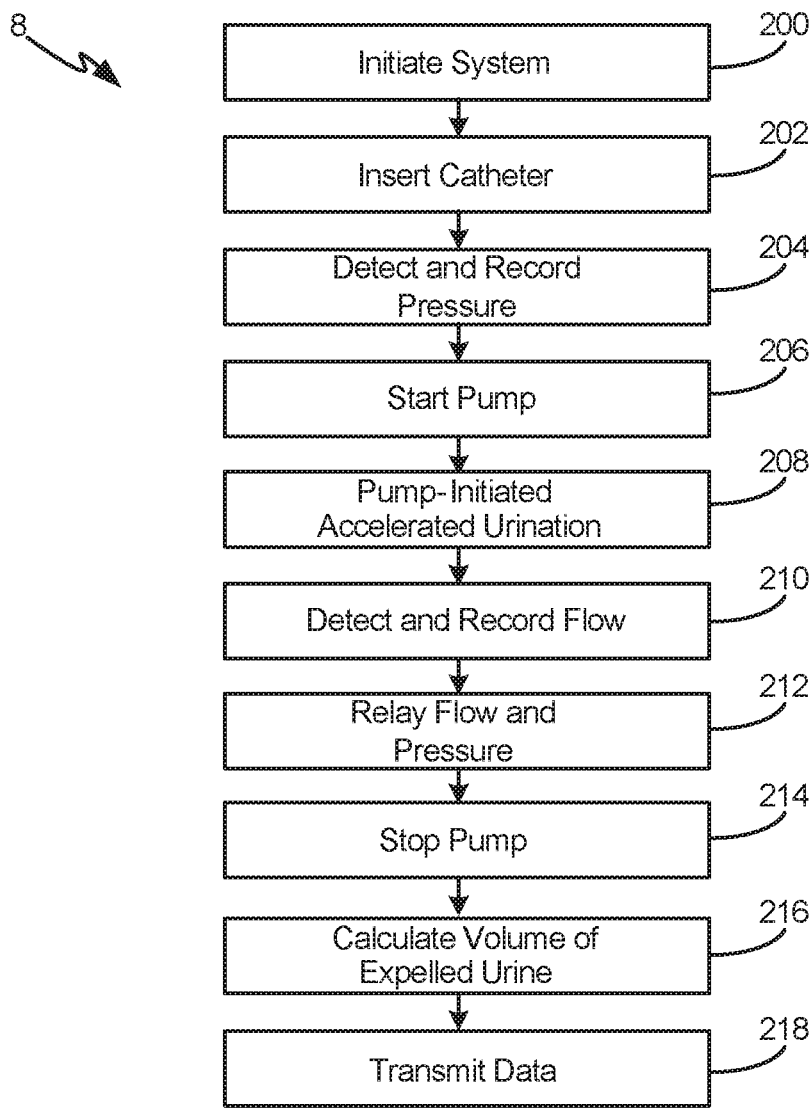

In operation, and as shown in FIG. 5, in certain implementations, after the system is initiated (box 200) and the catheter connected (box 202), the pressure can be detected and recorded (box 204). As a next step, the pump is turned on (box 206), thereby accelerating urination (box 208). Optionally, the flow rate can be detected and recorded (box 210), and the pressure and flow rates relayed to the processor (box 212). After urination has completed, the pump is stopped (box 214) and the volume of expelled urine can be calculated (box 216). Recorded data, such as pressure, flow, volume, time and the like, can be transmitted to the digital device (box 218).

In various embodiments, the pump 30 is used to accelerate the evacuation time of catheterization, maintain a constant negative pressure, and contribute to an almost constant flow rate of the fluid moving through the lumen.

Figure 6:
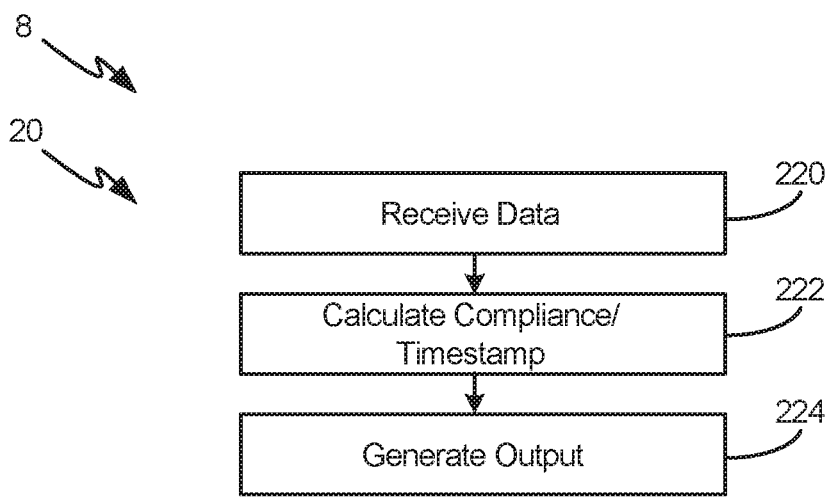
Figures 7, 8:
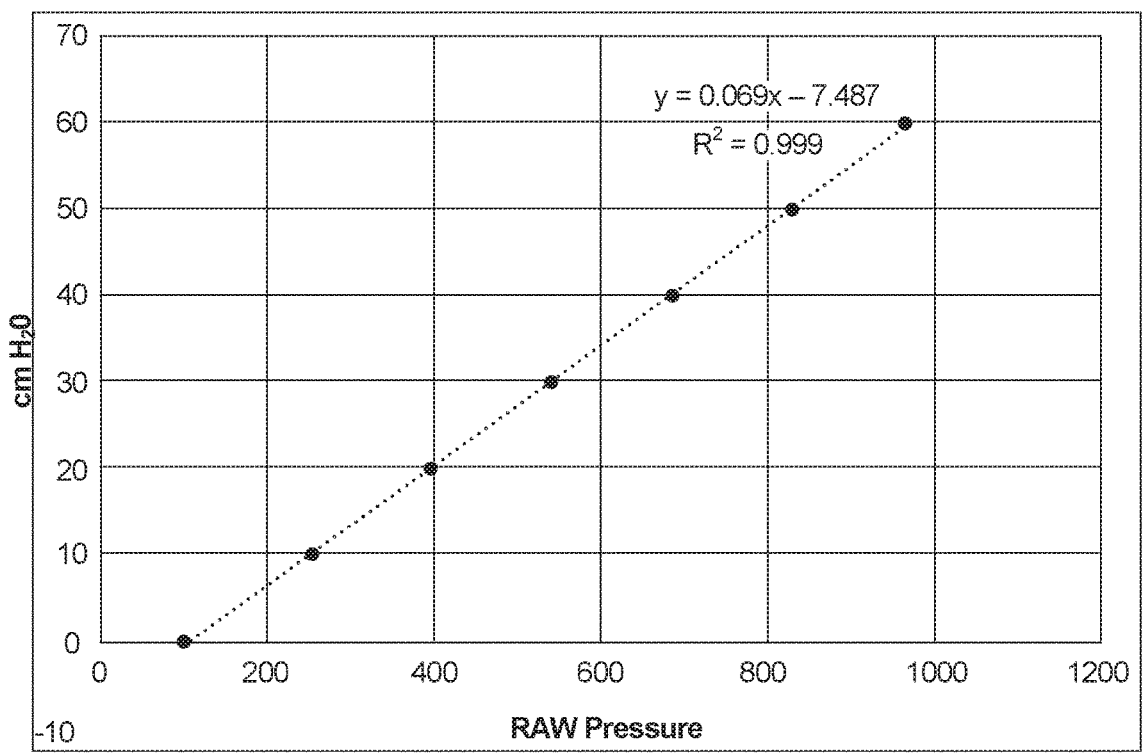
FIG. 7 shows an example comparison table of raw and actual pressure values
FIG. 8 shows an example scatter plot of raw and actual pressure values

As shown in FIG. 6, the data is received by the digital device (box 220). Optionally, additional calculations—such as compliance and trending—can be performed (box 222). The digital device is also able to generate output (box 224), which can be viewed by the patient, physician, or other interested party, such as by way of a mobile application or display device (not shown). In exemplary embodiments, the data can be transmitted by way of a secure connection over WiFi, Bluetooth™, or other known connection means to a third party at another location, such as a hospital, clinic, research or records institution, as has been previously described above. In certain implementations, this transmission is encrypted and can be achieved by way of cloud storage, the internet, and other known information transmission and storage methods. As would be apparent to one of skill in the art, the digital device 20 through a software application 25 can implement various steps to assist in obtaining, converting, packaging, and sending the resulted measurements to various users, as described elsewhere herein.

Returning to the implementations of FIGS. 2A-3B, in certain embodiments, a driver switch 36 can be provided to start the pump 30. For example, in certain embodiments, the driver switch 36 can be a chip switch driven by a small change in voltage and be configured to detect changes in light to detect the presence of fluid in the first lumen 16. In further embodiments, the driver switch 36 can be configured to interface with the processor and be capable of being toggled on and off based on pressure readings. In further examples, the driver switch can be operationally integrated with the valve 28, so as to operate the pump 30 in conjunction with opening the valve relative to the first lumen 16.

In further embodiments, and as shown in FIG. 2B, the pressure sensor component 18 can include a known pressure sensor 50, such as an AMS 5812-0008-D pressure sensor or other similar devices known to the skilled artisan. The pressure sensor 50 allows for high precision measurements and excellent drift and long-term stability. In various implementations, the pressure sensor component 18 and pressure sensor 50 can combine micro-machined, high quality piezoresistive measuring cells with a signal conditioning mixed-signal ASIC on a ceramic substrate. In exemplary embodiments, the pressure sensor 50 has physical storage media 52 such as an SD card reader and a clock 54 can also be in electronic communication with the pressure sensor 50 for recording and time-stamping the sensor readings. In various implementations, the clock 54 is a real time clock ("RTC") component configured to keep true time even when the CPU is asleep or shut down. In these embodiments, the CPU 40 is thus able to obtain true date and time data from the RTC 54 every time the device 10 is used.

In exemplary embodiments, other electronic components 56 such as printed circuit boards ("PCB") and a signaling mechanism 58, which can be an LED light, a buzzer, a LCD screen or other known device used to communicate to the user that a reading has been taken. These other electronic components 56 can be operationally integrated into the sensor component 18 as would be apparent to one of skill in the art.

In various embodiments, the pressure sensor component 18 and sensor 50 are specifically configured for applications with static and dynamic pressure measurements, barometric pressure measurement, vacuum monitoring, gas flow, fluid level measurement, and medical instrumentation. Accordingly, as shown in the implementation of FIG. 2A, the sensor component 18 is sensitive and reliable within the range of about 0.0—to about 60.0 cmH$_2$O, using a differential pressure measurement between current atmosphere and pressure detected within the lumen 24. As would be apparent to a skilled artisan, this is the range associated with urinary bladder pressures for the assessment of bladder health, and can accommodate the measurement of fluid pressure. It is also advantageous because the necessary components are durable and inexpensive. Further, in certain implementations, the sensor component 18 can have signal amplification circuitry configured to amplify the pressure output signal and clear the background noise from the signal. In these embodiments, a sensor battery 60 may also be provided. The battery can be a lithium-ion battery, though other types of battery are of course possible, such as powering the pressure sensor by way of the battery 34.

The pump 30 according to certain embodiments is also configured to calculate the volume that is expelled from the device 10 by detecting the volumetric flow rate and the elapsed time that the fluid is within the tube 14. Further, the pump 30 is configured to transmit the data relating to the volumetric flow rate and time to the CPU 40. In various embodiments, the volumetric flow rate the of pump 30 can be determined by power source testing, such as calculating the pump's 30 volumetric flow rate for different power source characteristics by measuring the amount of time required for a certain standard of volume to pass through the device, as would be apparent to one of skill in the art.

Bladder compliance can accordingly be calculated using the measured pressure and volume values obtained from the pressure and volume sensing components (such as the pressure sensor 18 and pump 30) of the device 10, respectively. In these embodiments, a function within the CPU 40 or an attached computer terminal can calculate bladder compliance by comparing the volume to the pressure and accounting for any calibrations, as discussed further below, in relation to Tables 1-5.

In certain implementations, the pump 30 has a flow meter to calculate volume. The flow meter calculated volumetric flow rate. Using the measured volumetric flow rate from the flow meter as well as the amount of elapsed time (the amount of time the device was in operation) measured by the CPU 40, to calculate the volume expelled from the device 10. This would be apparent to a skilled artisan. The pump 30 can be used to accelerate the evacuation time of catheterization, maintain a constant negative pressure, and contribute to an almost constant flow rate of the fluid moving through the lumen 16.

In exemplary implementations, and as shown in FIG. 3B, the pump 30 is a peristaltic pump configured to measure volume expelled from the bladder. As is known in the art, the mechanism of the peristaltic pump hinges on a set of rollers 70, 72 that compress the tubing 74 within the pump 30 to maintain a constant volumetric flow rate of the fluid 76 (shown by reference arrows A and B). In these implementations, the volumetric flow rate can be measured and used in conjunction with the amount of elapsed time (again, the amount of time the device was in operation) measured by the CPU 40 to calculate the total volume expelled from the device. In these implementations, the use of the peristaltic pump 30 provides a durable, low cost, and reliable measurement of volumetric flow rate. Further, the peristaltic pump 30 enables the propulsion of fluid from the catheter into the external environment (collection vessel) in a faster manner compared to catheter drainage by gravity.

To this end, and as shown in FIGS. 2A-3B, the pump 30 in certain implementations is configured to accelerate the catheterization process. That is, the power (electrical or otherwise) to the pump 30 can be increased to increase the volumetric flow rate of the pump 30, thereby increasing the flow rate of the fluid in the lumen 16. In those embodiments in which the pump 30 compresses and expands the tube 14 as described above, the increased action of the pump 30 causes the pump 30 to exert a more powerful suction on the fluid in the lumen 16. Regardless of the type of pump 30, the increased action of the pump 30 causes the pump to increase the flow rate of the fluid in the lumen 16, thereby applying greater suction to the fluid held in the bladder and urinary catheter. This suction will speed up the process by which the urine leaves the bladder via the urinary catheter. As such, in certain embodiments, the pump 30 can reduce the amount of time needed for urine to pass through the catheter and be eliminated into a collection vessel (not shown).

According to one embodiment, the pump 30 can be configured to decrease the amount of time needed to expel urine between about 0 and about 1500 mL of urine to less than about 10 minutes. Alternatively, the pump 30 can be configured to decrease the amount of time to less than about 5 minutes. In a further alternative, the pump 30 can be configured to decrease the amount of time to about 3 minutes.

The pump 30 in certain implementations can have a safety mechanism (not shown) in the form of a power switch that allows the patient or caregiver or another user) to turn the pump on or off as needed. Alternate embodiments include an automated switch to prevent power supply to the pump when the pressure sensor 18 detects certain pressures indicative of lumen 16 blockages or any indication that the flow of fluid through the device 10 has become impeded. An additional embodiment includes an automated switch to prevent power supply to the pump when there is any an indication that the lumen 16 is void of fluid (i.e. the bladder is empty). A further embodiment includes an automated switch that becomes activated and thus powers the bladder health monitoring system off with the passage of five minutes.

As discussed previously, in various implementations the device 10 also has a processor, or CPU 40. In one embodiment, the CPU 40 is an Arduino board. In one embodiment, the CPU 40 is a computer processing unit 40 or a central processing unit 40. Alternatively, the processor 40 can be a microprocessor, a computer, or any other known type of processor or processing unit that can be configured to assist with the operation of a medical device such as the device disclosed or contemplated herein. As shown in FIG. 1, in this embodiment, the processor 40 is operably coupled to both the pressure sensor component 18 and the pump 30 via wires 48 or other know types of physical connections. In further embodiments, and as shown in FIG. 2, a plurality of CPUs 40, 42 can be provided and operationally integrated with one another and the various components. More specifically, as shown in FIG. 2, the pump 30 is coupled to a first processor 40 directly, while the pressure sensor component 18 is coupled to a second processor 42 via more wires 49. Alternatively, the pressure sensor component 18 and pump 30 can be coupled to the processor 40 or processors 40, 42 wirelessly. FIGS. 2A-3A also show a voltage driver 38, which can also be operationally integrated with the CPU 40.

The processor 40 is configured to store the pressure data from the pressure sensor component 18, along with date and time data relating to the pressure data. Further, the processor 40 is also figured to calculate the volume expelled from the device 10 based on the volumetric flow rate and time data received from the pump 30, and further can store this volume data. In certain embodiments, the processor 40 is also configured to transmit the compliance, pressure, volume and other data wirelessly, or by direct connection, to the digital component 20 as discussed in further detail below. In one embodiment, the device 10 or the processor 40 has a transceiver (not shown) configured to communicate wirelessly, or by direct connection, with the digital component 20 such as a mobile device 20 or other separate system 20 as described above, thereby allowing for transmission of the data from the processor 40 to the system 20.

In certain embodiments, the processor 40 has software 25 (either integrated into the processor 40 or connectable with the processor 40 via a connection of some type) that can accomplish the various steps described herein, including saving pressure and volume, compliance measurements, such as volume and pressure, date, and time data on the processor 40 and outputting corresponding data or readings to the digital component 20 in real-time. A software application 25 can also be provided on the digital component 20. The processor 40 may also display the outputting pressure, volume, compliance, date, and time readings on a digital display 45 as part of the processor 40 and device 10. In a further embodiment, instead of a physical switch as described above, the software 25 can serve as an automated safety feature in the form of an automated switch that powers the pump on and off when, for example, fluid has ceased flowing through the first lumen 16, when certain pressure changes such as negative pressure is sensed by the pressure sensing component 50 and software 25, when the bladder health monitoring system has been in use for five minutes, when the device is inserted properly to a urinary catheter, or upon the satisfaction of other conditions, as would be apparent to one of skill in the art.

Further, it is understood that the CPU 40 can be configured via programming or software 25 to control and coordinate the operation of the sensor component 18 and the pump 30 to optimize operation of the system 8.

The digital component 20 of the system 8 is configured to communicate wirelessly with the processor 40. In one implementation, as mentioned above, the wireless communication utilizes Bluetooth™ technology through the communications components 62, 64. In one exemplary embodiment in which the digital component 20 is mobile device 21, the appropriate application in the device 21 can be configured to output the pressure and/or volume readings in any known form. Further, the digital component 20 can also be configured to store any of the pressure and/or volume, compliance, time, and date data as well.

As discussed above in relation to FIGS. 5-6, in certain embodiments the software application 25 is configured to output the time and date of each catheterization as well as a bladder pressure and bladder volume readings and bladder compliance. In addition, the application can also have an alarm function, providing feedback to the patient, caregiver, physician, or other person when a threshold is exceeded. For example, in one embodiment, if bladder pressure, volume and compliance readings worsen such that any or all of those parameters increase to the point of reaching a critical pressure or volume threshold indicative of bladder damage, then the mobile device application will trigger an alarm or notification of some kind, thereby causing the patient to consult his or her physician or take other appropriate steps. In addition, the alarm or notification of some kind can trigger the generation of an automatic electronic message to the treating physician, as well as upload a similar electronic message to the patient's file in a hospital's electronic medical record system. Alternatively, the application can be configured to trigger an alarm when one or more catheterizations are not performed in a timely fashion. This application can also permit the physician, caregiver, or patient to make adjustments to various settings, such as pump speed, catheterization thresholds and schedules, as well as pressure, volume, or compliance thresholds with the mobile device application.

Not only do the aforementioned neurogenic bladder patients benefit from this solution, but health care professionals, caregivers, and catheter distributing companies also reap advantages from such a device. The real-time measurement and data storage capabilities of the embodiments enable health care professionals such as physicians to have a means of regularly monitoring the patient's current bladder status without having to complete the invasive and time consuming office, hospital or clinical UDS test. For this same reason, patients benefit in having a system that monitors their condition so that if abnormal readings occur, they can consult their health care provider before irreversible damage to the bladder or renal system results. In addition, the amount of time that patient caregivers require to take patients to hospital clinics for appointments can be substantially decreased. Also, the amount of time that caregivers take to assist patients with catheterizing can be significantly decreased. Further, utilization of UDS testing by way of the present implementations can be reduced, thus reducing routine use of clinical UDS testing and reducing the overall treatment cost.

According to one embodiment, the various system embodiments described herein provide for measurement of pressure in the bladder at the time of catheter insertion. In accordance with other embodiments, the system 8 as described herein provides for earlier detection of harmful changes in bladder pressure, volume and compliance than known technologies, thereby triggering earlier intervention and protection of the kidney and bladder. In further implementations, the system can be used to assess the patient's compliance with a specified catheterization schedule by examination of the digital record of the timing of catheterization, or alert sent to the health care professional (such as a physician, physician assistant or nurse) when catheterization threshold does not fall within the optimal range set in the mobile device application. Further, adjustments in the frequency or timing of catheterization could also be made based on patterns of urine output and pressures. In additional implementations, this system is configured to permit patient self-monitoring of the patient's bladder health similar to a patient's home monitoring of blood pressure or blood sugars. The system 8 in certain embodiments is configured to notify a patient, caregiver, and/or physician about the status of a patient's bladder health, including whether the health of the bladder is improving, worsening, or staying the same. In this implementation, based on the information provided via the system 8, the physician or patient can intervene and adjust the patient's treatment regime to prevent bladder damage, if needed.

EXAMPLES

Below are examples of specific embodiments relating to the calibration and operation of the disclosed bladder monitoring devices, systems and methods. They are provided for illustrative purposes only, and are not intended to limit the scope of the various embodiments in any way.

FIGS. 7-12 depict various examples and implementations of the disclosed system 8 being calibrated. One example of the device 10 involves the use of the aforementioned AMS 5812-0008-D pressure sensor. Calibration testing can be performed to ensure that the pressure values read from the sensor component 18 are within a predetermined level of accuracy. For example, the accuracy threshold can be set at about 5 percent of the true pressure reading.

As shown in Table 1, and Chart 1, a water column apparatus (from 0 to about 70 cm $H_2O$) can be used to compare the actual true reading of pressure (as measured via the column, shown as "Tested Pressure") with the raw value obtained from the pressure sensor component 18.

In this example, the pressure sensor component 18 is used to obtain dynamic relative pressures between the measuring nozzle and the baseline nozzle of the catheter. The CPU 40 obtained an average initial raw pressure reading from the pressure sensor component 18 by reading the raw output from the pressure sensor component 18 every 0.1 second for 10 pressure readings. This raw pressure reading is then converted to a $cmH_2O$ scale using a function described by calibration testing of the device 10 using three different catheter sizes, a water column, and experimental $cmH_2O$ water column values between 0-70 $cmH_2O$. From these results, a person skilled in the art can readily derive a calibration equation to address reading variability created by varying catheter sizes.

To this end, as shown in Tables 2-5, ten trials were conducted on a variety of catheter types (male/female, catheter length, catheter lumen diameter): 16 French ("Fr") 16 inch male catheter, 16 Fr 6 inch female catheter, 14 Fr 6 inch female catheter, and 10 Fr 10 inch male catheter. From the observed pressure readings for each trial, it was possible to establish calibration equations for the various catheter sizes and lengths. Since there can be slight differences in the pressure readings between different catheter lengths and diameters, an equation was determined for each catheter type listed above, as would be apparent to one of skill in the art.

Accordingly, in order to improve accuracy of the pressure sensing unit, the raw data acquired during the calibration testing in tandem with the actual true readings obtained from the water column can be used to construct a mathematical equation with a correction factor to further improve the accuracy of the system 8 in various implementations. As would be apparent to one of skill in the art, these calibration equations can be programmed into the processing unit 40 that communicates with the pressure sensing component 18.

As shown in Tables 1-5, in the present examples, the results when analyzed from the calibration testing showed that the constructed pressure sensing unit (the AMS 5812-0008-D pressure sensor and the associated circuitry) was able to reliably detect pressure readings within the desired range (0-70 cm $H_2O$) within five percent of the actual value.

The total expelled volume is calculated by the CPU 40 using the total time elapsed multiplied by a function representing the constant pump 30 flow rate, this function was described by pump 30 and power source testing where the constant flow rate of the pump 30 was tested against many different power source characteristics.

Therefore, in various implementations, shown variously in FIGS. 1-6, in one example the processor or processors (shown at 40 and 42) collect data values from the various components—such as the pressure sensor 18, pump 30 and clock 54. In these embodiments, the CPU 40 or CPUs 40, 42 can collect true date and time data from the clock component 54, dynamic pressure readings from the pressure sensor component 18 and flow from the pump 30.

In one exemplary implementation, the CPU 40 has software configured to record date and time values within the software application 25 on the digital device 20 as data points. In this implementation, the pressure sensor component 18 is used to obtain dynamic relative pressures between the second lumen 24, which is in fluid communication with the first lumen 16, thereby collecting a pressure reading directly from the catheter via the catheter coupling 12, and the measured atmospheric pressure. The CPU 40 obtains an average initial RAW pressure reading from the sensor component 18 by reading the RAW output from the pressure sensor component 18 every 0.1 second for 10 pressure readings. This RAW pressure reading is then converted to a $cmH_2O$ scale using a function described by calibration testing of the device using three different catheter sizes, a water column, and many experimental $cmH_2O$ water column values between 0-70 $cmH_2O$ shown in Tables 1-5.

In this example, the CPU 40 records this $cmH_2O$ pressure value as the second data point of the software application 25. As another step, the CPU 40 obtains the total volume expelled by the device 10 during use by measuring the time the pump 30 is being supplied power. In this embodiment, the patient/user presses a digital button connected to the CPU 40 and the CPU 40 provides a low voltage to the bridge driver component 38. The driver component 38 is used for output voltage control and after the low voltage stimulus provided to the driver component 38 from the CPU 40, the driver component 38 delivers a large output voltage to the pump 30 so long as the low voltage stimulus remains. In a subsequent step, the CPU 40 starts an internal timer when delivering the low voltage to bridge driver component 38. In this implementation, the pump 30 is stopped by the timer or when a low voltage stimulus is presented by a physical/ digital or automatic switch, as would be apparent to one of skill in the art. The timer then records the total time elapsed when the pump 30 was under power from the driver component 38. The CPU 40 records this total expelled volume value as the last data point of the software application 25. In this embodiment, the CPU 40 then records the software application 25 to an SD card 52 or transmits the software application 25 wirelessly to the digital device 20 by way of a communications component 62, as described elsewhere. As would be apparent to one of skill in the art, other implementations are possible.

Although the present invention has been described with reference to preferred embodiments, persons skilled in the art will recognize that changes may be made in form and detail without departing from the spirit and scope of the invention.

What is claimed is:

1. A bladder monitoring system comprising:
   (a) a housing;
   (b) a first elongate tube comprising a first lumen;
   (c) a catheter coupling component disposed at a distal end of the first elongate tube, the catheter coupling component comprising an opening in fluid communication with the first lumen, wherein the catheter coupling component is constructed and arranged to be coupleable to a urinary catheter such that the opening is in fluid communication with a lumen of the urinary catheter, the urinary catheter being a single lumen catheter;
   (d) a pressure sensor disposed within the housing and in fluid communication with the catheter coupling component via a proximal end of the first elongate tube;
   (e) a processor disposed within the housing and operably coupled to the pressure sensor; and
   (f) a communications component operably coupled to the processor,
   wherein the bladder monitoring system is constructed and arranged to detect bladder pressure at the time of catheterization.

2. The system of claim 1, further comprising a second elongate tube comprising a second lumen capable of fluidic communication with the catheter coupling component by way of a second opening.

3. The bladder monitoring system of claim 2, further comprising a valve constructed and arranged to control fluid communication between the catheter coupling, the first elongate tube and the second elongate tube.

4. The system of claim 1, wherein the communications component is constructed and arranged to wirelessly transmit the detected bladder pressure.

5. The system of claim 1, wherein the first lumen is in fluid communication with the pressure sensor and the second lumen is in fluid communication with a pump constructed and arranged to evacuate a patient bladder.

6. The bladder monitoring system of claim 5, wherein the pump is constructed and arranged to operate when in fluid communication with the catheter coupling.

7. The bladder monitoring system of claim 4, wherein the pump is further constructed and arranged to transmit data relating to a flow rate to the processor.

8. The bladder monitoring system of claim 7, further comprising a digital device comprising an application constructed and arranged to measure bladder compliance from the pressure sensor and the flow rate.

9. The bladder monitoring system of claim 8, wherein the digital device is constructed and arranged to display the bladder compliance measurement.

10. The system of claim 1, wherein the pressure sensor is constructed and arranged to collect dynamic relative pressures in the catheter.

11. A bladder health monitoring system comprising:
    (a) a bladder monitoring device comprising:
        (i) a first elongate tube comprising a first lumen;
        (ii) a catheter coupling component disposed at a distal end of the first elongate tube, the catheter coupling component comprising an opening in fluid communication with the first lumen;
        (iii) a pressure sensor in fluidic communication with the catheter coupling component;
        (iv) a communications component in communication with the pressure sensor; and
        (v) a second elongate tube comprising a second lumen capable of fluidic communication with the catheter coupling component by way of a second opening; and
    (b) a digital device constructed and arranged to wirelessly communicate with the bladder monitoring device via the communications component, the digital device comprising an application constructed and arranged to output pressure or volume readings from the bladder monitoring device,
    wherein the catheter coupling component is constructed and arranged to couple to a single lumen urinary catheter such that the opening is in fluid communication with a lumen of the urinary catheter, and
    wherein the bladder health monitoring system is constructed and arranged to detect pressure at the time of catheterization.

12. The bladder health monitoring system of claim 11, wherein the bladder monitoring device further comprising the communications component is a transceiver.

13. The bladder health monitoring system of claim 11, wherein the pressure sensor is constructed and arranged to detect pressure within the lumen and transmit data relating to the pressure to the processor.

14. The bladder health monitoring system of claim 11, further comprising a pump in fluidic communication with the catheter coupling component and constructed and arranged to evacuate a patient bladder.

15. The bladder health monitoring system of claim 14, wherein the pump is further constructed and arranged to detect the volumetric flow rate of the fluid within the first lumen and transmit data relating to volumetric flow rate to the processor.

16. The bladder health monitoring system of claim 15, wherein the application is constructed and arranged to measure bladder compliance from the pressure sensor and volumetric flow rate.

17. The bladder health monitoring system of claim 16, wherein the digital device is constructed and arranged to display the bladder compliance measurement.

18. The bladder health monitoring system of claim 11, further comprising a valve constructed and arranged to control fluid communication between the catheter coupling, the first elongate tube, and the second elongate tube.

19. A catheterization bladder health monitoring system, comprising:
    (a) a housing;
    (b) a first elongate tube comprising a first lumen disposed through the housing;
    (c) a single lumen catheter coupling component disposed at a distal end of the first elongate tube and outside the housing, the catheter coupling component comprising an opening in fluid communication with the first lumen;

(d) a communications component;
(e) a second elongate tube comprising a second lumen capable of fluidic communication with the catheter coupling component by way of a second opening; and
(f) a pump in fluidic communication with the single lumen catheter coupling component and constructed and arranged to evacuate a patient bladder, to detect the volumetric flow rate of the fluid within the first lumen, and transmit data relating to the volumetric flow rate to a processor, wherein:
(i) the single lumen catheter coupling component is constructed and arranged to be coupled to a urinary catheter such that the opening is in fluid communication with a lumen of the urinary catheter, the urinary catheter being a single lumen catheter, and
(ii) the bladder health monitoring system is constructed and arranged to sense bladder pressure.

* * * * *